(12) United States Patent
Hsu

(10) Patent No.: US 6,358,731 B1
(45) Date of Patent: Mar. 19, 2002

(54) STERILIZABLE CULTIVATION SYSTEM WITH SEPARATELY ATTACHABLE MICROFILTRATION MEMBRANE

(76) Inventor: Wei K. Hsu, 113 Highway 24, Commerce, TX (US) 75429

( * ) Notice: Subject to any disclaimer, the term of this patent is extended or adjusted under 35 U.S.C. 154(b) by 0 days.

(21) Appl. No.: 09/422,030

(22) Filed: Oct. 20, 1999

(51) Int. Cl.[7] ............................................. C12M 1/12
(52) U.S. Cl. ......................... 435/297.5; 435/297.1; 435/304.1; 47/1.1
(58) Field of Search .................... 47/1.1; 435/297.1, 435/297.5, 304.1

(56) References Cited

U.S. PATENT DOCUMENTS

| | | | | |
|---|---|---|---|---|
| 4,203,445 A | * | 5/1980 | Jessup et al. | |
| 4,878,312 A | * | 11/1989 | Shimizu | 47/1.1 |
| 5,659,997 A | * | 8/1997 | Sprehe et al. | 47/1.1 |
| 5,681,630 A | * | 10/1997 | Smick et al. | 428/40.1 |

FOREIGN PATENT DOCUMENTS

JP 09275773 A * 10/1997

* cited by examiner

*Primary Examiner*—David A. Redding
(74) *Attorney, Agent, or Firm*—Sherman D. Pernia

(57) ABSTRACT

A sterilizable cultivation system is provided for growing selected organisms for use in biological applications and the cultivation edible fungi. A sealable, sterilizable container holds a growth substrate in a sterile condition. A separate, adhesive vent filter is provided, which is adhereable to a vent opening in the container. The vent filter is gas permeable and allows gas exchange between the interior of the container and the ambient environment, but prevents the passage of microbes and other organisms into or out of the container. This gas exchange prevents excess carbon dioxide from accumulating in the container and allows necessary oxygen into the container in order to maintain an appropriate growth environment for the selected organisms. The vent filter may be combined with the container (a) during manufacture of new containers, or (b) in the field by the end-user on new containers or on re-cycled containers. The separately provided vent filters allow the end-user to adjust certain parameters of the growth environment within the container in the field. This is accomplished by adjusting the venting characteristics of the cultivation system, by increasing or reducing the amount and quality of the vent filters on the container.

20 Claims, 3 Drawing Sheets

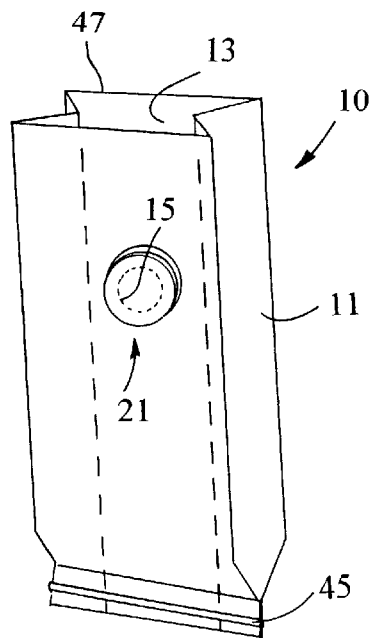
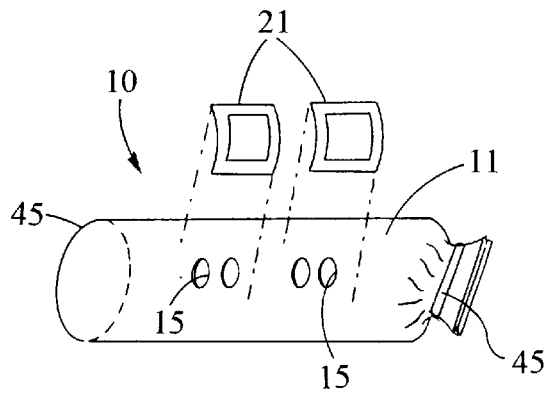
Fig. 1A
Fig. 1B
Fig. 2
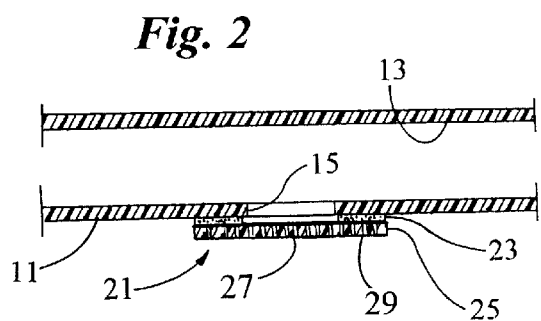
Fig. 3
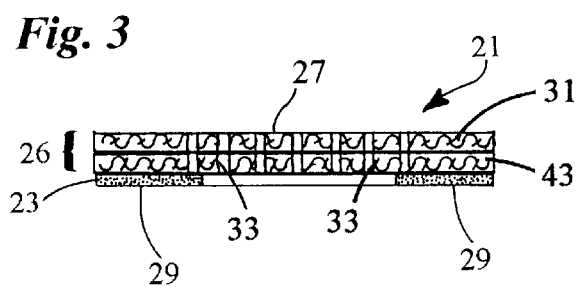

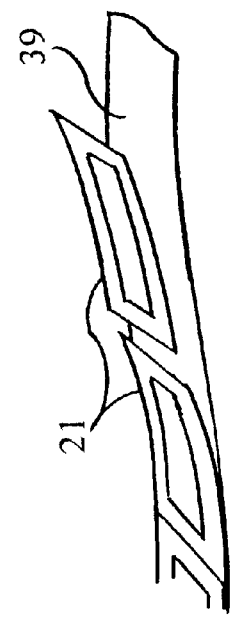
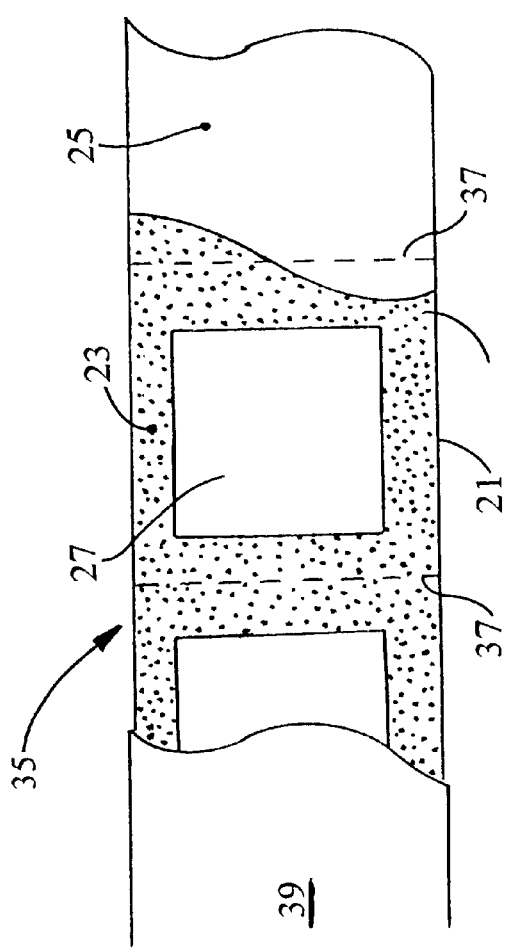

STERILIZABLE CULTIVATION SYSTEM WITH SEPARATELY ATTACHABLE MICROFILTRATION MEMBRANE

The present application claims the benefit of prior filed China Applications, serial numbers 98 2 29711.4 and 98 2 29712.2, both filed Oct. 21, 1999 to which the present application is a regular U.S. national application.

FIELD OF THE INVENTION

The present invention is in the field of sterilizable cultivation containers for growing selected organisms in isolation from the ambient environment. More specifically, it relates to a microfiltration membrane that is separately adhereable to a sterilizable cultivation container. In particular, the present invention relates to such containers for the cultivation of edible fungi.

BACKGROUND OF THE INVENTION

Aerobic organisms during growth require oxygen and produce carbon dioxide. In order to grow and maintain a pure strain of a selected organism, it is advantageous to exclude competing organisms, including microorganisms, from the growth environment as well as maintain the proper oxygen to carbon dioxide ratio. Sterilizable cultivation containers provide this advantage. Such containers are used extensively for the cultivation of edible mushrooms. Much of this cultivation is accomplished using plastic pouches or bags. However, the cost of bags and pouches can represent a high percentage of total raw material cost, which encourages the recycling of the bags and pouches. In order to provide proper venting when using recycled cultivation containers, growers often resort to cotton vent plugs, which are inherently less reliable or controllable than desired.

Control of the internal growing environment of the cultivation container is important, and the field has been motivated to address this issue. For example, U.S. Pat. No. 5,230,430, noting that it is desirable to maintain moisture content, attempts to provide a method for moisture control. However, the '430 patent does not teach a means for modifying the moisture conditions once the container is in use in the field to increase moisture loss. Also, the manufacture of the container of the '430 patent is complicated in that it requires the integration of a filter element into an otherwise ordinary plastic bag during the course of manufacture of the bag. Also, because of the integrated filter element of the '430 bag and similar cultivation containers, the ability to recycle containers is reduced.

It would be beneficial to have a sterilizable cultivation system wherein the moisture loss can be controllably increased or decreased in the field. Additionally, it would be advantageous to be able to use ordinary manufactured plastic bags as cultivation containers, and to be able to recycle them.

SUMMARY OF THE INVENTION

The present application claims the benefit of prior filed China Applications, serial numbers 98 2 29711.4 and 98 2 29712.2, both filed Oct. 21, 1999, the content of which are incorporated herein by reference.

The present invention is a sterilizable cultivation system for growing a homogeneous population of a selected organism on a growth supporting substrate. The system is useful in agricultural and biological applications where isolation of the growing organism from the general environment is desirable. The system is advantageous for preventing contamination of the growing organisms from competing organisms present in the environment, and for preventing exposure to the environment from the organisms being cultivated. The present cultivation system is particularly useful for the growing of edible mushrooms, but is useful also for the growth of other fungi, nematodes, and similar organisms that are desirable to grow in isolation.

The present invention comprises a sealable container, the interior of which holds a substrate suitable for growing the selected organism after it is inoculated onto the substrate. The container is capable of holding the substrate in a sterile condition, meaning that: (a) sterile substrate can be added to the container and kept sterile, or (b) substrate can be added to the container and subsequently made sterile. The container itself should be relatively impervious to the ambient environment and substantially gas impermeable. In order to support the growth of aerobic organisms, the container has at least one vent or breathing hole to allow gas exchange between the interior of the container and the ambient environment outside of the container. A separate breathing filter is adhered to the container to cover the vent/breathing hole. The filter allows gas transmission or exchange of gases between the interior of the container and the ambient environment, while not allowing passage or transmission of microbes. A layer of a non-water soluble, pressure sensitive adhesive is posited between the container and the breathing filter. The adhesive layer provides for closely adhering the filter to the container, thus isolating the vent hole and interior of the container from the ambient environment.

The breathing filter is typically constructed in a flat or planar configuration, and has a central area and a periphery. The peripheral area is for receiving or contacting the adhesive layer when adhering the filter to the container, and the central area is for gas exchange and filtration. The vent holes in the container are to covered individually or in multiples using one or more breathing vent filters. The filters are provided separately from the container, as individual unit items or in multiples, such as where multiple breathing filters are arranged at their periphery, as in a series or an array, and wound into a roll or provided in sheets. The filters can be individually removed from a sheet or roll for adhering to the container. This allows the filters to be placed on the container by the end-user in the field. In this way, the end user may recycle the container for more than one cultivation cycle. Die-cuts and perforations or the like can be provided in the filter material to facilitate removing individual filters from a roll or sheet.

The breathing filter includes a microfiltration membrane. The microfiltration membrane has micron and smaller sized pores or breathing holes to excludes microbes (including fungi and bacteria) from passing into or out of the container. The breathing pore holes range in size from about 1.0 $\mu$m to 0.05 $\mu$m in diameter. Preferably, the breathing pores are evenly distributed on the micro filter breathing membrane, and preferably range from about 1.0 $\mu$m to 0.3 $\mu$m in diameter. The amount of the breathing filter's central area available for gas exchange and filtration is modifiable by covering the microfiltration membrane with an occlusive agent (such as adhesive tape, paint or the release paper).

The adhesive layer of the present invention is made of a pressure sensitive adhesive for closely adhering the breathing filter to the container. In order to facilitate recycling of the container, it is desirable that the adhesive layer be releaseable from the container. Also, for some applications, it is desirable that the adhesive used in the adhesive layer is both releaseable from and re-adhereable to the container.

Appropriate adhesives having these qualities are known to and selectable by one of ordinary skill in the art of adhesives. The advantage of an adhesive layer that is both releaseable from and re-adhereable to the container is that inoculation of sterile substrate held in the container with a selected organism can be accomplished through the vent hole without substantial compromise of the sterility of the cultivation system.

The adhesive layer is covered by a release material, which is removable from the adhesive layer prior to adhering the filter to the container. Such release materials include silicone release paper, a release coating and other adhesive release means known to one of ordinary skill in the art. When the adhesive layer is combined with the breathing filter, it is applied or coated only on the periphery of the filter, in a wide enough pattern to assure close adhesion of the filter to the container.

The separate breathing filter of the present invention may be constructed as a laminate of a microfiltration membrane and a support material, to help protect the membrane and to give the breathing filter added strength and durability. The support material can be made of any of a number of openly porous materials known to the ordinary skilled artisan, including polymer based, cellulose based or other fiber based or non-woven materials. The adhesive layer can be applied directly to the breathing filter laminate as described above. Alternatively, the periphery of the vent hole in the container can provide a surface area for contacting the adhesive layer. In this case, the adhesive layer is applied to the container separately from the breathing filter, and is protected prior to use with a release paper or similar means as disclosed above.

An individual filter laminate may include a central area of variable size. The user can peel off increasingly larger concentric, pre-scored areas of adhesive to expose similarly larger central areas of the microfiltration membrane.

The sterilizable cultivation system of the present invention anticipates that the sealable container may take a variety of constructions in that it may be rigid, semi-rigid or very flexible. Likewise, it may have a variety of configurations, such as a bag, a cylinder, bottle or box. Preferably, the container is a bag formed from a length of flexible tubular material and sealable at both ends to provide a sealable container. In order to accomplish the bag being recyclable, at least one of the sealable ends is un-sealable and re-sealable, allowing the bag to be re-used. For the growing of mushrooms and the like where the ability to inspect the contents of the container is desirable, the container can be made of clear or semi-transparent materials.

The exact composition of the growth substrate of the present invention is dependent on the selected organism it is desirable to cultivate. Generally, the starting substrate is a mixture of solid particles and nutrients suitable for growing the selected organism.

BRIEF DESCRIPTION OF THE DRAWINGS

FIG. 1A is a perspective view of a gusseted bag or pouch type container of the present invention.

FIG. 1B is a frontal view of a tube type container of the present invention.

FIG. 2 is a side cross-sectional view of the container of FIG. 1 detailing the features of an attached breathing filter over a vent hole.

FIG. 3 is a cross-sectional view of a laminated breathing filter showing the different layers.

FIG. 5A is a top view of an array of adhesive vent filters arranged at their periphery in a series on a tape, such as can be wound into a roll.

FIG. 5B is a perspective drawing showing how individual vent filters, provided as a continuous series tape, might be removed from a roll such as described in FIG. 5A.

DETAILED DESCRIPTION OF THE INVENTION

Figure 4:
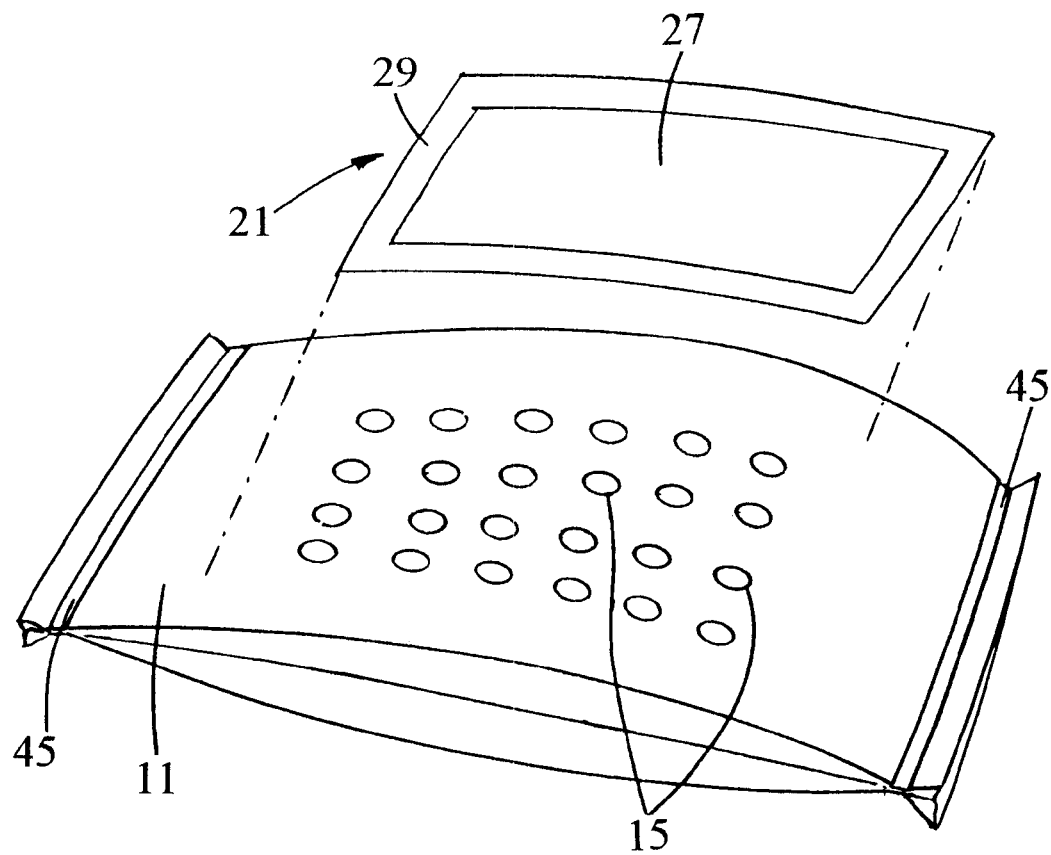
FIG. 4 shows the relationship between a sealed bag-type cultivation container with a plurality of breathing vent holes and an adhesive breathing vent filter for covering the vent holes.

Referring now to the figures, FIGS. 1A and 1B show the sterilizable cultivation system 10 of the present invention as a bag or pouch type container and as a semi-rigid tube type container for containing a growth substrate (not shown). The sterilizable cultivation system 10 is useful in the growing of selected organisms for biological applications and mushroom cultivation. The cultivation system comprises a sealable container 11 having an interior 13 for holding the growth substrate in a sterile condition. Typically, the container 11 is constructed of a gas impermeable material, and has at least one breathing or vent hole 15 to allow gas exchange between the interior 13 of the container 11 and an outside ambient environment. The container 11 holds a growth substrate suitable for supporting growth of the selected organisms when inoculated onto the substrate.

As shown in FIGS. 1A, 1B and 2, a separate adhesive breathing vent hole filter 21 is adhereable to the container 11 to cover the vent/breathing holes 15 in the container 11. FIG. 2 shows a cross-section of a separate adhesive vent hole filter 21 adhered to the outside surface of a container 11. The breathing vent hole filter 21 has an inner layer 23 and an outer layer 25. The outer layer 25 is a filter layer for allowing gas transmission and exchange, while not allowing microbe transmission through the filter 21. The inner layer 23 is a layer of a non-water soluble, pressure sensitive adhesive for closely adhering the vent filter 21 to the container 11. The close adhesion of the vent filter 21 to the container 11 isolates opening of the vent/breathing hole from the ambient environment outside of the container 11.

Breathing vent hole filters 21 are flat, flexible and "fabric-like" in their handling properties. As shown in FIGS. 2 & 3, a breathing vent hole filter 21 has a central area 27 and a peripheral area or periphery 29, The filter central area 27 is the location on the breathing vent hole filter 21 that provides for allowing gas transmission and exchange, while not allowing microbe transmission. The filter periphery 29 is the location on the breathing vent hole filter 21 of the inner layer 23 that comprises the adhesive for adhering the filter to the container 11. The adhesive for adhering the filter to the container is coated on the periphery 29, and the pattern of adhesive coated on the periphery becomes the inner layer 23. The inner layer 23 adhesive allows the adhesive vent hole filter 21 to be closely adhered to the container 11 to cover the breathing vent holes 15 in the container 11.

In an alternative to the preferred embodiment, the breathing vent hole 15 on the container 11 has a periphery area (not shown) on the surface of the container 11 surrounding the vent hole 15 for receiving an adhesive layer for adhering the filter to the container and allowing gas transmission and filtration.

The adhesive vent hole filter 21 of the present invention may be provided in a large range of sizes as suites as end-users need. The overall size of an individual vent hole filter 21 may be small relative to the size of the container 11 to which it is adhered, as in FIG. 1B. Alternatively, the overall size of an individual vent hole filter 21 may be large relative to the size of the container 11 to which it is adhered, as in FIG. 4.

The separate adhesive breathing vent hole filters 21 of the present invention may be provided individually and in bulk, in bulk being as a plurality of individual units arrayed at their periphery. As an example, in this latter configuration, numbers of the filters 21 may be laid out as shown in FIG. 5A, in a series 35, or in an array for winding into a roll, or for cutting or fan-folded into sheets. Vent hole filters 21 may be removed individually from a bulk means by cutting (if a continuous series), by tearing (if pre-scored or perforated 37) or by peeling (if pre-cut), and adhered to a container 11 by a provider of containers or by an end-user of the present cultivation system 10. To facilitate accomplishing this feature of the present invention, the inner layer 23 adhesive is covered by a release material 39, which release material 39 is removable from the inner layer 23 adhesive distributed on the periphery 29 of the vent filter 21 prior to adhering the filter 21 to the container 11. The release material 39 can be any of a number of adhesive release means known to one of ordinary skill in the art, including a silicone release paper, a release coating and other such means.

In the preferred embodiment, the outer layer 25 of the breathing vent filter 21 of the present invention comprises a microfiltration membrane 31, the microfiltration membrane 31 having micron and smaller sized breathing pore holes 33, which are too small to allow microbes, including fungi and bacteria, into or out of the container 11. The microfiltration membrane, 31 has breathing pores 33 ranging in size from about 1.0 $\mu$m to 0.05 $\mu$m in diameter. The breathing pores 33 are substantially evenly distributed on the micro filter breathing membrane 31. Preferably, breathing pores 33 range in size from 1.0 $\mu$m to 0.2 $\mu$m in diameter. Selection of the size of the breathing pores 33 depends on the size of the organisms to be filtered, and whether and how much the size of the breathing pores 33 will change (if at all) if the filter 21 is subjected to a particular heat sterilization process.

It is a feature of the preferred embodiment of the adhesive breathing vent filter 21 of the present invention shown in FIG. 3, that a filter outer layer comprises a laminate 26 of a microfiltration membrane 31 and an openly porous membrane support material 43, such as a non-woven polymer based, cellulose based or other fiber based support material. An inner adhesive layer 23 is provided on the periphery 29 of the laminate 26 as in the above embodiment of the breathing vent filter 21. The addition of the membrane support material 43 gives the adhesive breathing vent filter 21 increased strength and durability. Such filter materials combining microfiltration membranes with a support material are commercially available (e.g., CELGARD, by Hoechst Celanese).

It is also preferred that the inner layer 23 of the adhesive breathing vent filter 21 comprise an adhesive for adhering the filter 21 to the container 11, which adhesive is then releaseable from the container 11. Also, it is preferred that after the adhesive inner layer 23 of the filter 21 is released from the container 11, that the filter 21 be re-adhereable to the container 11.

The amount of the central area 27 of a vent hole filter 21 that is available for gas exchange may be modified by covering it with an occlusive agent, such as adhesive tape, paint or the release paper. Additionally, adhesive vent hole filters may be provided with a feature that allows the area available for gas exchange to be modified.

The container 11 of the present invention is sealable and sterilizable, to provide for maintaining its contents in a sterile condition. In its preferred embodiment, the sterilizable cultivation system 10 of the present invention comprises a sealable container 11 that is a bag or pouch (see FIGS. 1A & 4), or a tube (see FIG. 1B). However, other embodiments of the container 11 are anticipated and practicable to the ordinary skilled artisan. These types of sealable containers are formed from a length of tubular material and sealable at both ends of the tube. The containers 11 shown in FIGS. 1A & 1B and 4, have their ends sealed by means of a heat seal 45. In the preferred embodiment, the container 11 has at least one of the sealable ends that is un-sealable and re-sealable, allowing the bag to be re-used. This can be accomplished by cutting the heat seal 45 from the end of the container 11 to form an open end 47 and re-heating the opened end to form a new heat seal 45. It is preferred that the sealable container 11 of the present invention be made of a semi-transparent material. The container 11 may be constructed of flexible, semi-rigid and rigid materials.

Typically, the sterilizable cultivation system 10 of the present invention is utilized when it is desirable to cultivate a selected organism without competition from other organisms, or to prevent the cultivated organism having access to the ambient environment. The present sterilizable cultivation system 10 is useful for cultivating organisms such as fungi, nematodes and any organism capable of growing on the growth substrate. The growth substrate typically comprises a mixture of solid particles and nutrients for growing the selected organism. Specific formulations of nutrient substrate are known in the art and practicable by the ordinary skilled artisan.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A sterilizable cultivation system for growing selected organisms for use in biological applications and the cultivation of edible fungi comprising:
   a sealable container having an interior for holding a growth substrate in a sterile condition, the container being gas impermeable and having at least one vent hole to allow gas exchange between the interior of the container and an outside of the container, and the growth substrate suitable for supporting growth of the selected organisms when inoculated onto the substrate; and
   an adhesive breathing vent filter having an outer layer and an inner layer, the vent filter being separately adhereable to the container to cover the vent hole in the container, the outer layer being a filter material for allowing gas exchange while not allowing microbe transmission, and the inner layer being an adhesive material of non-water soluble, pressure sensitive adhesive for closely adhering the vent filter to the container and isolating the vent hole and the interior of the container from the ambient environment outside of the container.

2. The breathing vent filter of claim 1 wherein the filter material has a periphery and a central area, the periphery for receiving the adhesive material of the inner layer, the adhesive material for adhering the vent filter to the container, and the central area for covering the vent holes and allowing gas exchange and filtration.

3. The breathing vent filter of claim 2 wherein a plurality of breathing filters are arrayed at their periphery, and provided wound into a roll and in sheets, and individual vent filters are removable from an array for adhering to the container.

4. The breathing vent filter of claim 2 wherein the filter layer comprises a microfiltration membrane, the membrane having micron and smaller sized breathing pores preventing microbes from passing into or out of the container.

5. The filter layer of claim 4 wherein the microfiltration membrane, has pores ranging in size from about 1.0 $\mu$m to 0.05 $\mu$m in diameter, which pores substantially are evenly distributed on the microfiltration membrane.

6. The adhesive breathing vent filter of claim 1 wherein the adhesive material for adhering the filter to the container is releaseable from the container.

7. The adhesive breathing vent filter of claim 1 wherein the adhesive material for adhering the filter to the container is releaseable from and re-adhereable to the container.

8. The adhesive breathing vent filter of claim 1 wherein the adhesive material is covered by a release material, which release material is removable from the adhesive layer prior to adhering the filter to the container.

9. The adhesive breathing vent filter of claim 8 wherein the adhesive material is covered by a release material, which release material is selected from the group consisting of: a silicone release paper, a release coating and other adhesive release means known to one of ordinary skill in the art.

10. The adhesive breathing vent filter of claim 2 wherein the adhesive material for adhering the filter to the container is coated on the periphery.

11. The adhesive breathing vent filter of claim 2 wherein the outer layer comprises a laminate of a microfiltration membrane and a porous support material, to give the filter increased strength and durability.

12. The container of claim 1 wherein the vent hole has a vent hole periphery, the vent hole periphery for receiving an adhesive layer for adhering the vent filter to the container and allowing gas transmission and filtration.

13. The sterilizable cultivation system of claim 1 wherein the sealable container is a bag.

14. The sealable container of claim 1 wherein the sealable container comprises a length of tubular material and is sealable at both ends of the length of tubular material.

15. The bag of claim 14 wherein at least one of the sealable ends is un-sealable and re-sealable, allowing the bag to be re-used.

16. The sealable container of claim 13 wherein the sealable container is a bag made of a semi-transparent material.

17. The sterilizable cultivation system of claim 1 wherein the sealable container is constructed of a rigid material.

18. The sterilizable cultivation system of claim 1 wherein the selected organism is any organism desired to be cultivated without competition from other organisms.

19. The sterilizable cultivation system of claim 1 wherein the selected organism is chosen from the group consisting of fungi, nematodes and any organism capable of growing on the growth substrate.

20. The adhesive breathing vent filter of claim 1 wherein the central area of the filter layer for gas transmission and filtration is modifiable by covering it with an occlusive agent, such as adhesive tape, paint or a release paper.

* * * * *